United States Patent [19]

Rice

[11] Patent Number: 4,681,308
[45] Date of Patent: Jul. 21, 1987

[54] DIAGNOSTIC PATIENT SUPPORT APPARATUS

[76] Inventor: Paul Rice, Corp. 300 Foster St., Littleton, Mass. 01466

[21] Appl. No.: 890,803

[22] Filed: Jul. 24, 1986

Related U.S. Application Data

[63] Continuation of Ser. No. 755,667, Jul. 16, 1985, abandoned.

[51] Int. Cl.⁴ .......................................... A61G 13/00
[52] U.S. Cl. ................................... 269/322; 378/209
[58] Field of Search .................... 269/322–325, 269/326, 328; 378/208, 209

[56] References Cited

U.S. PATENT DOCUMENTS

| | | | |
|---|---|---|---|
| 2,910,259 | 10/1959 | Johnson | 269/328 X |
| 3,227,439 | 1/1966 | Carlson | 269/325 |
| 3,227,440 | 1/1966 | Scott | 269/326 |
| 3,397,411 | 8/1968 | Rossi | 378/209 X |
| 3,452,977 | 7/1969 | Ryman | 269/324 |
| 3,650,523 | 3/1972 | Darby, Jr. | 378/208 X |
| 3,751,028 | 8/1973 | Scheininger et al. | 269/328 X |
| 3,797,819 | 3/1974 | Platz et al. | 269/322 |
| 3,868,103 | 2/1975 | Pageot et al. | 269/325 |
| 3,967,128 | 6/1976 | Smulewicz | 378/208 X |
| 4,101,120 | 7/1978 | Seshima | 269/323 |
| 4,195,829 | 4/1980 | Reser | 269/325 |
| 4,475,072 | 10/1984 | Schwehr et al. | 269/323 X |
| 4,552,346 | 11/1985 | Schnelle et al. | 269/322 |

*Primary Examiner*—Frederick R. Schmidt
*Assistant Examiner*—Steven P. Schad
*Attorney, Agent, or Firm*—Wolf, Greenfield & Sacks

[57] ABSTRACT

A diagnostic patient support structure including a base and a table top structure. The table top structure includes a central section for supporting the patient's torso and discrete leg extension sections diverging therefrom at an acute angle for supporting the patient's respective legs.

9 Claims, 7 Drawing Figures

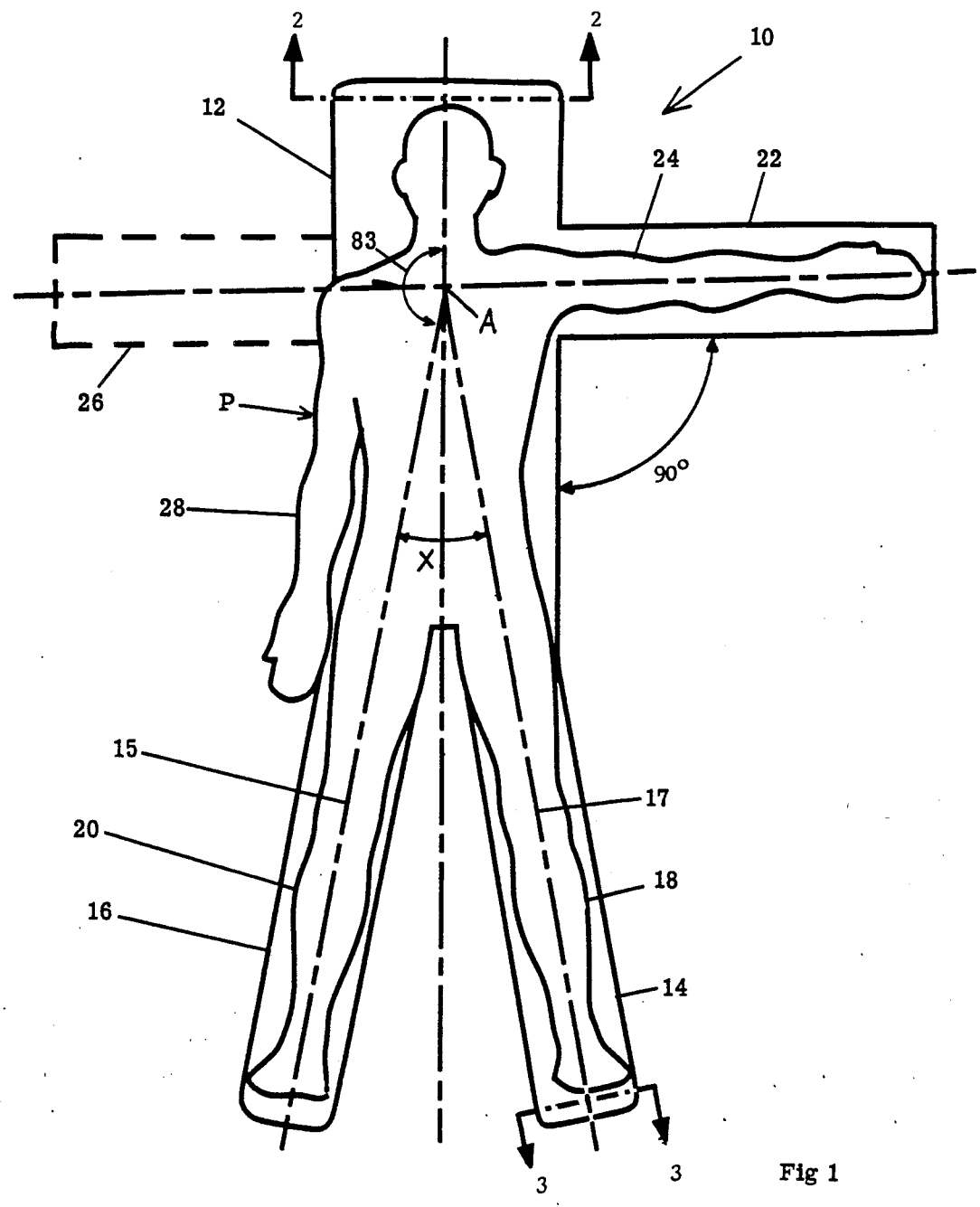
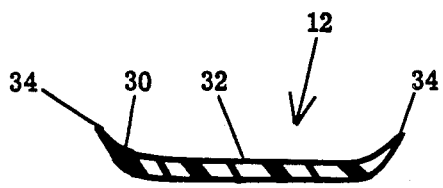
Fig 2
Fig 3

DIAGNOSTIC PATIENT SUPPORT APPARATUS

This is a continuation of application Ser. No. 755,667 filed July 16, 1985 now abandoned.

BACKGROUND OF THE INVENTION

This invention relates to a diagnostic patient support apparatus and more particularly to an apparatus for supporting patients undergoing nuclear magnetic resonance (NMR) and other medical testing.

Conventional tables used to support patients during NMR testing are typically large, expensive and complicated to maneuver. Additionally, they do not conveniently permit inspection of just one limb at a time. For example, when a conventional table is inserted into the NMR device both legs are invariably exposed to NMR testing even though a diagnosis is required for only one of the legs. Therefore, portions of the body are needlessly exposed to NMR testing. Additionally, the analysis or imaging of more than one part of the anatomy at the same time is not as accurate from a clinical standpoint as an independent analysis of separate parts of the anatomy.

A patient support structure has been proposed which employs separate parallel supports for each of the patient's legs. However, that structure is not readily maneuverable and does not conform well to the human anatomy because a person's legs are not parallel; rather they diverge from the torso. Accordingly, these structures have not provided comfortable or satisfactory support for patients undergoing NMR testing.

It is, therefore, an object of this invention to provide an improved diagnostic patient support apparatus which permits the patient's appendages to be individually subjected to medical testing.

It is a further object of this invention to provide a diagnostic support apparatus which may be easily, quietly and conveniently operated and maneuvered. It is a further object of this invention to provide a diagnostic patient support structure which eliminates the need for accessory mounting rails.

It is a further object of this invention to provide a diagnostic patient support structure which is particularly suitable for supporting patients and their individual appendages for NMR testing.

It is a further object of this invention to provide a diagnostic patient support structure which does not intefere with the electromagnetic field generated by an NMR testing device.

SUMMARY OF THE INVENTION

This invention results from a realization that individual NMR testing of each of a patient's limbs may be accomplished by providing, for each of the respective limbs, discrete supports which are secured apart such that their axes intersect at a central axis of the patient, and from the further realization that the maximum spacing which is practicable and comfortable for the legs is provided by diverging discrete limb supports so that they generally conform to the human anatomy.

Accordingly, this invention features a diagnostic patient support apparatus which includes a base and a table top mounted on the base. The table top includes a central section for supporting the patient's torso and discrete leg extension sections connected to the central section and diverging therefrom at an acute angle for supporting the patient's legs.

In a preferred embodiment the central section includes a concave upper surface for receiving the patient's torso. At least one of the central and/or extension sections may include a concave upper surface for receiving a respective leg. The leg extension sections typically diverge at a 20° angle or at a substantially similar angle (e.g. 10°–30°). Such spacing enables individual legs to be inserted one at a time into diagnostic equipment without inteference from other parts of the table top.

A third extension section may be connected to the central section and extend therefrom for supporting one of the patient's arms and may also include a concave upper surface for receiving that arm. Typically the third extension section is connected to the central section at substantially a 90° angle. A fourth, and typically similar, extension section may be connected to the other side of the central section for supporting the patient's other arm.

Most preferably the table top structure includes a central axis point defined by the intersection of the axes of two or more of the extension sections. Preferably, the axes of the extension sections intersect at a common point on the central section. The table top structure may be rotatably mounted on the base, most preferbly at the central axis point for rotation therearound. The base is typically provided with a wheel mechanism enabling movement of the table top structure toward and away from a diagnostic NMR apparatus in conjunction with which the apparatus is primarily intended for use. Rotatable mounting of the table top structure at the central axis point allows the various limb extension sections to be aligned and inserted in the diagnostic apparatus by straight back and forth movement of the table top along a path perpendicular to the apparatus. Where the table top structure is rotatably mounted at such a central axis point, the wheel mechanism is preferably mounted on a straight track mechanism aligned perpendicular to the diagnostic apparatus, and each extension section having an axis intersecting such a central axis point may be inserted into the diagnostic apparatus by a simple combination of rotation of the table top and straight back and forth movement along the track mechanism.

The upper surfaces of one or more of the central and/or extension sections may be provided with a mechanism for receiving the various limbs and/or torso of the patient in order to prevent lateral movement on the table top surface. The mechanism on the table top surfaces for receiving the patient typically comprises a concavity or upward projections on the table top surface conforming to the shape of the portion of the patient to be received. In a most preferred embodiment where the table top structure comprises a non-magnetically interactive material such as glass, fiberglass, ceramic, wood, plastic and the like, various surfaces of the table top structure may be pre-molded or otherwise shaped by conventional means to conform to the shape of the patient's torso and/or limbs.

The apparatus may be provided with a mechanism for driving the apparatus along the path of the track mechanism, and where wheel mechanisms are provided, such wheels engage the track mechanism and are guided therealong a predetermined path toward and away from the diagnostic apparatus. Alternatively, but less preferred, the apparatus may be provided with conventional rotatable wheel mechanisms on the base for movement of the apparatus in essentially any motion, back and forth and sideways, relative to the diagnostic device.

Apart from the table top structure, the materials comprising any part of the apparatus coming into interactive adjacency with the diagnostic electromagnetic field of the diagnostic apparatus used in conjucntion therewith, do not include magnetic or magnetically attractive materials which would interfere with an electromagnetic field of the diagnostic device.

BRIEF DESCRIPTION OF THE DRAWINGS

Other objects, features, and advantages will be apparent from the following detailed description of preferred embodiments taken in conjucntion with the accompanying drawing in which:

FIG. 1 is a simplified top view of a table top according to the invention with a patient supported thereon;

FIG. 2 is a cross sectional view of the central section taken along line 2—2 of FIG. 1;

FIG. 3 is a cross sectional view of the second extension section taken along line 3—3 of FIG. 1;

DETAILED DESCRIPTION OF PREFERRED EMBODIMENTS

Figure 4:
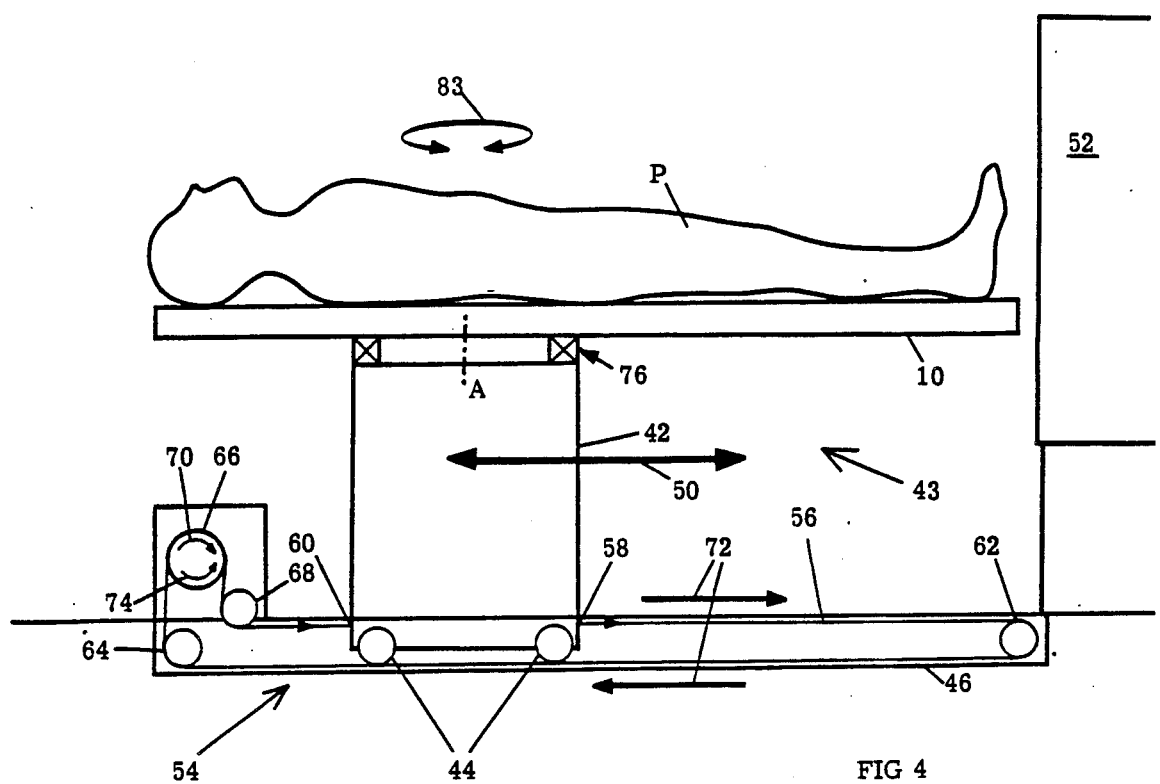
FIG. 4 is a simplified schematic diagram of the diagnostic patient support apparatus according to the invention.

There is shown in FIG. 1 a table top 10 suitable for use in the diagnostic patient support apparatus of this invention. A central section 12 supports patient P's head and torso. A pair of extension sections 14 and 16 are integrally connected with central section 12 and diverge therefrom at an angle X, preferably about 10°-30° and most preferably about 20°, whereby the longitudinal axes 15 and 17 of sections 14 and 16, respectively, diverge at that angle from a central axis point A corresponding to that point of the human torso from which legs 18 and 20 diverge. Patient P's legs 18 and 20 are spread apart and supported by sections 14 and 16, respectively. A twenty degree angle X (plus or minus about 10 degrees) is approximately the angle at which a human's legs when spread apart have axes e.g. 15, 17 which intersect at a central axis point between the chest and the head.

A third extension section 22 is integrally (or removably) connected at a 90° angle to central section 12 for providing support for patient P's arm 24. A similar fourth extension section 26, shown in phantom, may be employed for supporting arm 28. Alternatively, when testing of arm 28 is desired patient P may be rolled over so that arm 28 is supported by section 22. The combination of connecting extensions 14 and 16 at an angle X of between about 10 and about 30 degrees and connecting extension 22 at an angle of about 90 degrees results in the axes of all three extensions 14, 16, 22 intersecting at the common central axis point A. Such common central axis point allows the option of rotatably connecting the table top 10 to a base structure at the central axis thereby enabling a minimal amount of manipulation of the table top 10 for purposes of inserting a particular limb, 18, 20, or 24 into an NMR apparatus for analysis of the particular limb.

As shown in cross section in FIG. 2, central section 12 includes a concave upper surface 30 and in particular features a substantially flat intermediate region 32, having a width of approximately sixteen inches and curled up edges 34. The width from edge to edge is approximately twenty inches. Concave surface 30 conveniently receives the patient's head and torso and eliminates the need for mounting rails along the edges of central section 12. As indicated in FIG. 3, extension sections 14 and 16 are also provided with concave upper surfaces 36. The extension sections are approximately four to six inches wide from edge to edge. Additionally each extension section preferably cross sectionally forms an arc of a circle having a diameter of approximately eight inches. This enables the extension section to fit into a typical analysis opening of a standard NMR device. The extension sections 22, 28 which support the patient's arms are constructed similarly to the leg supporting extension sections 14 and 16.

All portions of table top 10 are compoesed of a non metallic and non-ferrous substance such as glass, fiberglass, ceramic, wood, plastic or other resin. The use of carbon is also typically avoided in the table top.

As shown in FIG. 4 table top 10 is mounted to a table base 42 to form table apparatus 43. The base is typically composed of aluminum and includes support bearings 44 which engage a track 46. More specifically, each bearing, FIG. 5, includes a pair of plastic wheel or roller elements 44a, 44b disposed on opposite sides of base 42 and connected by an axle 48 which extends through the base. Track 46 consists of a pair of elongated aluminum rails 46a, 46b which receive respective wheel or roller elements 44a, 44b and permit table apparatus 43 to roll back and forth in the direction of doubleheaded arrow 50, FIG. 4, toward and away from NMR machine 52 along a simple straight line path substantially perpendicular to the machine 52.

A drive system 54, FIG. 4, may be provided for moving table apparatus 43 along track 46. That system includes a drive belt 56 attached at the forward and rearward ends 58 and 60 of base 42. Belt 56 extends from forward end 58 between the rails 46a, 46b, around idler pulley 62, back through rails 46a, 46b, and beneath base 42. The belt then engages roller puller 64 and drive motor 66 and is directed toward idler puller 68 to rearward end 60 of base 42. In operation motor 66 is operated in the direction of arrow 70 to draw belt 56 in the direction of arrows 72. This pulls table apparatus 42 toward NMR machine 52. To pull the table apparatus away from machine 52 motor 66 is driven in the opposite direction of arrows 70, i.e. in the direction of arrows 74.

Figure 6:
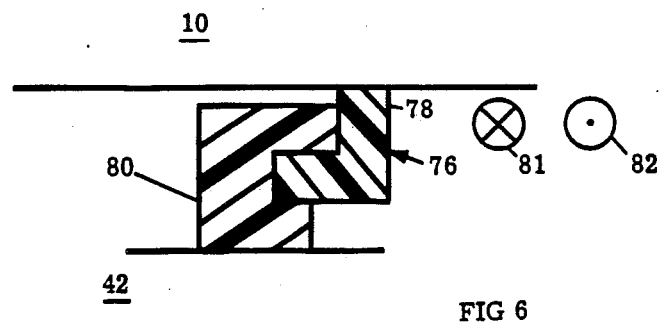
FIG. 6 is a cross sectional view of a portion of a pivotable bearing between a table top and a base structure according to the invention.

Table top 10 and base 42 are pivotably interconntected by an annular pivot bearing 76. As shown in greater detail in cross-section in FIG. 6 bearing 76 includes a first annular element 80 a c-shaped cross section which is mounted to base 42 and receives element 78. The mating elements 78 and 80 have complementary surfaces comprising plastic, bronze, or other suitable non-magnetic bearing material which enables element 78 to slide in the directions of arrows 81 and 82 relative to element 80. This permits table top 10 to pivot in the directions of doubleheaded arrow 83 about a pivot point A, FIGS. 1 and 4.

In operation NMR testing is performed by retracting table apparatus 43 to the end of track 46 which is distant from NMR machine 52, FIG. 4. Central section 12 of table top 10 is generally axially aligned with the diagnostic opening 86, FIG. 7, of machine 52. Patient P is placed on the table top as previously described. The table top is then pivoted approximately 10° in the direction of arrow 88 so that leg extension section 16 is generally aligned with opening 86 and table apparatus 43 is driven forward along track 46 to insert leg extension section 16 and the leg 20 it supports into diagnostic opening 86. Diagnostic NMR testing is then performed on leg 20 alone. Meanwhile extension section 14 and the leg 18 it supports are inserted into non-diagnostic auxilliary opening 90 and leg 18 is protected from the potentially harmful effects of the NMR diagnosis occurring within opening chamber 86.

Following completion of testing of leg 20 table apparatus 43 is retracted along track 46 to withdraw section 16 and leg 20 from opening 86. Table top 10 is then pivoted around central axis point A approximately 20° in the direction of arrow 92 to align extension section 14 and leg 18 with opening 86. The table apparatus is driven forward to insert section 16 and leg 20 into opening 86 where the leg is diagnosed. Section 16 and leg 20 are meanwhile inserted into non-diagnostic auxillary opening 94.

After both of the patient's legs have been tested his arms may be examined by withdrawing the patient from the NMR machine and pivoting table top 10 approximately 90° in the direction of either arrow 88 or arrow 92. This aligns the respective arm supporting extension sections 26 and 22 with diagnostic opening 86 so that the arms may be inserted for testing as previously described. Due to the preferred orientation of extension sections 22 and 26 of about 90° to central section 12 the arms are easily inserted without interference from any other part of table top 10.

Figure 5:
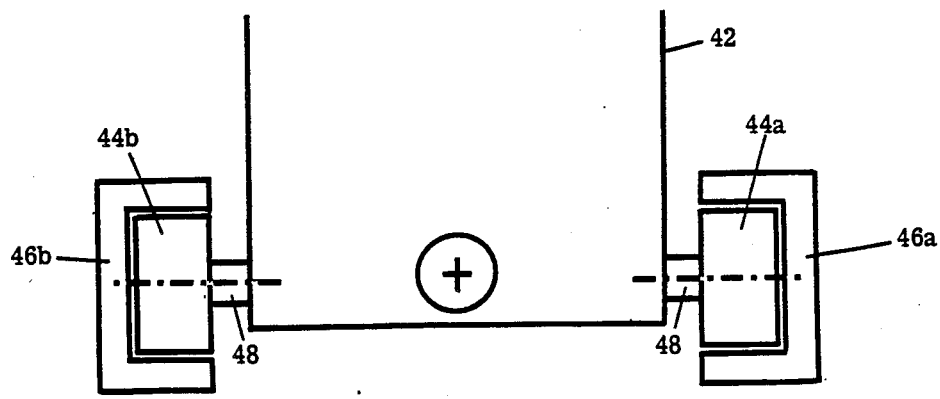
FIG. 5 is a cross sectional view of the track and wheel engagement area of the device of FIG. 4.
Figure 7:
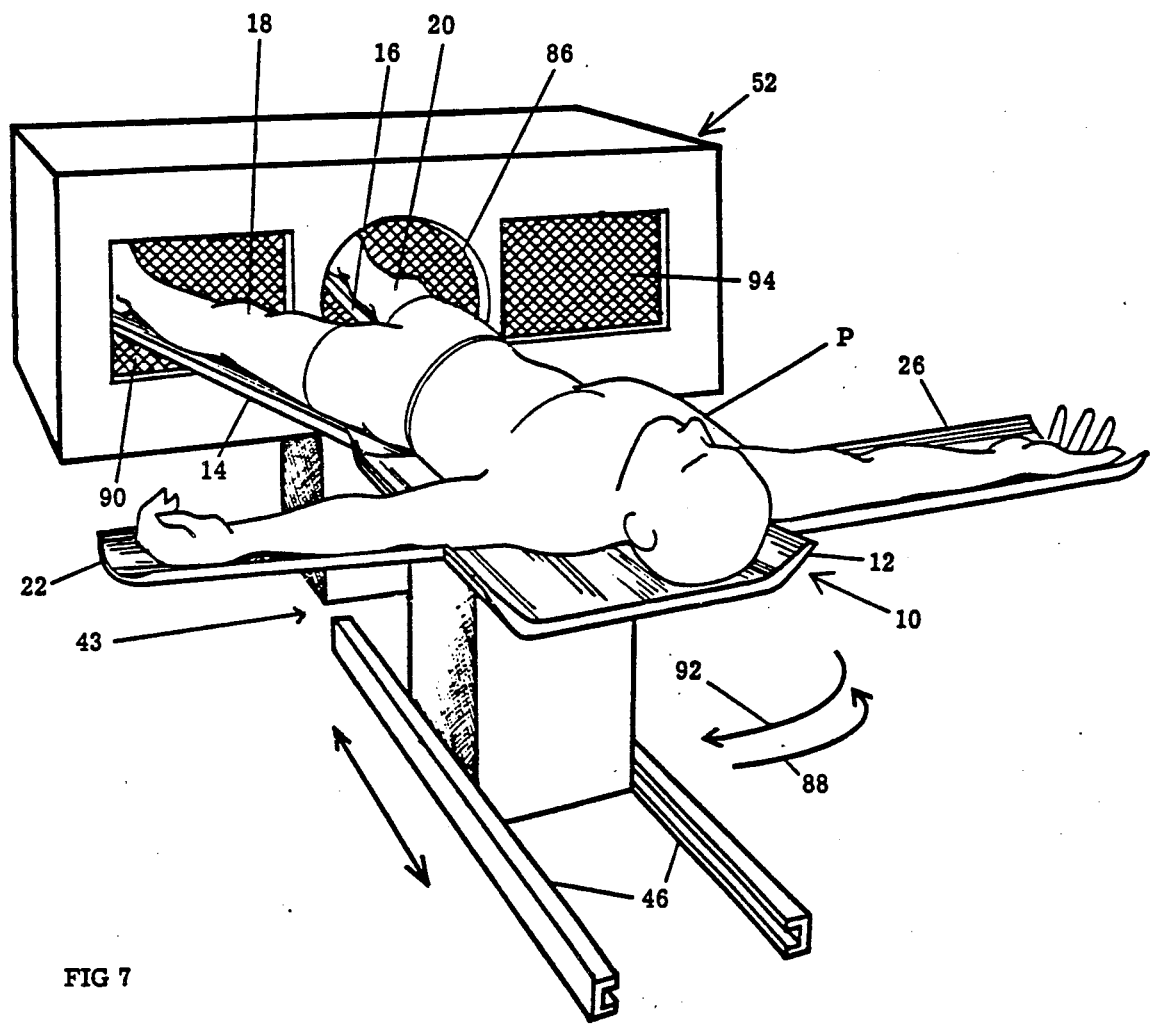
FIG. 7 is an isometric view of the diagnostic patient support apparatus supporting a patient during testing by a NMR device.

Rotatable mounting of the table top 10 to the base 42 at central axis point A, FIGS. 1, 4 enables the use of the simple straight line track means 46, FIGS. 4, 5, 7 in lieu of a track having a more complicated path whereby the table top 10 and base 42 would have to be movable sideways relative to the NMR machine 52 in order to individually align each extension section 14, 16, 22 and/or 26 with diagnostic opening 86.

Alternatively base 42 could be provided with rotatable wheel means and the track could be eliminated thereby allowing the entire base 42 and table top 10 structure to be movable around any desired path on the floor. The straight lined path track 46 is preferred, however, both for purposes of eliminating movement of the patient during analysis by NMR machine 52 and for purposes of simplifying manipulation of the table 10 and base 42.

Because iron and other magnetic metals and carbon are not used in the table top, apparatus 43 does not interfere with the electromagnetic field generated by the NMR device 52.

It will now be appareent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A diagnostic patient support apparatus comprising:
a base; and
a table top structure rotatably mounted on said base at a central axis point corresponding to about the center of the chest area of a patient the table top including a central section for supporting the patient's torso, discrete leg extension sections connected to said central section and diverging therefrom at an acute angle for supporting the patient's respective legs, at least one arm extension section connected to said central section and extending therefrom at about a right angle for supporting at least one of the patient's arms;
wherein the axes of said leg extension and said arm extension sections intersect at about the central axis point on said table top structure;
said base including wheel means mounted in a track means travelling toward and away from a diagnostic machine for moving said apparatus solely along the travel of said track means toward and away from said diagnostic machine.

2. Apparatus in accordance with claim 1 wherein said leg extension sections diverge from each other at an angle of about 20 degrees.

3. Apparatus in accordance with claim 2 wherein one or more of said central and extension sections include means disposed on the upper surface thereof for receiving the patient's torso or limbs thereby preventing lateral movement of said patient on said structure.

4. Apparatus in accordance with claim 1 further including means for driving said base along said track means.

5. A diagnostic patient support apparatus comprising:
a table top structure including a central section for supporting the patient's torso and limb extension sections connected to said central section for supporting the patient's limbs, wherein said limb extension sections include two leg extension sections diverging from each other at an acute angle and at least one arm extension section, said limb extension sections each having an axis intersecting at about a central axis point corresponding to about the center of the chest area of a patient; and
a base rotatably mounted to said table top structure at said central axis point, said base including wheel means mounted in a track means travelling toward and away from a diagnostic machine for moving said apparatus solely along the travel of said track means toward and away from said diagnostic machine.

6. Apparatus in accordance with claim 5 wherein said leg extension sections diverge from each other at an angle of about 20 degrees.

7. Apparatus in accordance with claim 5 wherein one or more of said central and extension sections include means disposed on the surface of said table top structure for receiving the patient's torso and limbs thereby preventing lateral movement of said patient on said structure.

8. Apparatus in accordance with claim 5 wherein said arm extension section is connected to said central section at an angle of about 90 degrees.

9. Apparatus in accordance with claim 5 further comprising means for driving said base along said track means.

* * * * *